(12) United States Patent
Baldessarini et al.

(10) Patent No.: US 6,747,029 B2
(45) Date of Patent: Jun. 8, 2004

(54) DOPAMINE $D_4$ RECEPTOR ANTAGONISTS AS TREATMENT FOR ATTENTION DEFICIT-HYPERACTIVITY DISORDER

(75) Inventors: Ross J. Baldessarini, Newton, MA (US); Kehong Zhang, Waltham, MA (US); Frank I. Tarazi, Woburn, MA (US)

(73) Assignee: The McLean Hospital Corporation, Belmont, MA (US)

( * ) Notice: Subject to any disclaimer, the term of this patent is extended or adjusted under 35 U.S.C. 154(b) by 0 days.

(21) Appl. No.: 10/096,673

(22) Filed: Mar. 12, 2002

(65) Prior Publication Data

US 2002/0187920 A1 Dec. 12, 2002

Related U.S. Application Data

(60) Provisional application No. 60/275,198, filed on Mar. 12, 2001.

(51) Int. Cl.[7] .................................................. A61K 31/497
(52) U.S. Cl. ........................... 514/252.12; 514/253.04; 514/253.06; 514/254.02; 514/255; 514/316; 514/426
(58) Field of Search ....................... 514/252.12, 253.04, 514/255, 316, 426, 253.06, 254.02

(56) References Cited

U.S. PATENT DOCUMENTS

| | | | |
|---|---|---|---|
| 5,576,319 A | 11/1996 | Baker et al. | 514/253 |
| 6,335,326 B1 | 1/2002 | Den Hartog et al. | 514/212 |

OTHER PUBLICATIONS

Belliotti et al., "A Series of 6– and 7–Piperazinyl–and –Piperidinylmethylbenzoxazinones With Dopamine $D_4$ Antagonist Activity: Discovery of a Potential Atypical Antipsychotic Agent" J. Med. Chem., 42(25):5181–5187 (1999).
Bristow et al., "L–745,870, A Subtype Selective Dopamine $D_4$ Receptor Antagonist, Does Not Exhibit A Neuroleptic–Like Profile in Rodent Behavioral Tests" J. Pharmacol. Exp. Ther., 283(3):1256–1263 (1997).
Broderick et al., "Clozapine, Haloperidol, and The $D_4$ Antagonist PNU–101387G: in vivo Effects on Mesocortical, Mesolimbic, and Nigrostriatal Dopamine and Serotonin Release" J. Neuro. Transm., 105:749–767 (1998).
Feldpausch et al., "The Role of Dopamine $D_4$ Receptor in The Induction of Behavioral Sensitization to Amphetamine and Accompanying Biochemical and Molecular Adaptations" J. Pharmacol. Exp. Ther., 286(1):497–508 (1998).
Goldman et al., "Diagnosis and Treatment of Attention–Deficit/Hyperactivity Disorder in Children and Adolescents" JAMA, 279:1100–1107 (1998).
Jentsch et al., "Dopamine $D_4$ Receptor Antagonist Reversal of Subchronic Phencyclidine–Induced Object Retrieval/Detour Deficits in Monkeys" Psychopharmacology 142(1):78–84 (1999).
Leung et al., "Vascular Endothelial Growth Factor is a Secreted Angiogenic Mitogen" Science 246:1306–1309 (1989).
Okuyama et al., "A Selective Dopamine $D_4$ Receptor Antagonist, NRA0160: A Preclinical Neuropharmacological Profile" Life Sci., 65(20):2109–2125 (1999).
Patel et al., "Biological Profile of L–745,870, A Selective Antagonist with High Affinity for The Dopamine $D_4$ Receptor" J. Pharmacol. Exp. Ther. 283:636–647 (1997).
Sanner et al., "Synthesis, SAR and Pharmacology of CP–293,019: a Potent, Selective Dopamine $D_4$ Receptor Antagonist" Bioorg. Med. Chem. Lett., 8(7):725–730 (1998).
Seeman et al., "Atypical Neuroleptics Have Low Affinity for Dopamine $D_2$ Receptors or are Selective for $D_4$ Receptors" Neuropsychopharmacology 16:93–110 (1997).
Sunahara et al., "Cloning of The Gene for A Human Dopamine $D_5$ Receptor With Higher Affinity for Dopamine Than $D_1$" Nature 350:614–619 (1991).
Tarazi et al., in "Dopamine $D_4$ Receptors: Significance for Molecular Psychiatry at the Millennium", Molecular Psychiatry, 4:529–538 (1999).
Zhang et al. "Effects of Dopamine $D_4$ Receptor–Selective Antagonists on Motor Hyperactivity in Rats with Neonatal 6–hydroxydopamine Lesions" Psychopharmacology, 161:100–106 (2002).
Zhang et al., "Plasticity of Dopamine $D_4$ Receptors in Rat Forebrain: Temporal Association with Motor Hyperactivity Following Neonatal 6–hydroxydopamine Lesioning" Neuropsychopharmacology 26(5):625–633 (2002).
Zhang et al., "Role of Dopamine $D_4$ Receptors in Motor Hyperactivity Induced By Neonatal 6–Hydroxydopamine Lesions In Rats" Neuropsychopharmacology 25(5):624–632 (2001).
Faraci et al., "The Discovery of Potent and Selective Dopamine $D_4$ Receptor Antagonists", *Next Generation Therapeutics, Current Opinion in Chemical Biology*, 2:535–540, (1998).
Kula et al., "Neuropharmacological Assessment of Potential Dopamine $D_4$ Receptor–Selective Radioligands", *European J. of Pharmacology*, 367:139–142, (1999).
Zhuang et al., "Hyperactivity and Impaired Response Habituation in Hyperdopaminergic Mice", *PNAS*, 98:(4); 1982–1987, (2001).
Oak et al., "The Dopamine D4 Receptor: One Decade of Research," *European Journal of Pharmacology*, 405:303–327, 2000.
Zhang et al., "Role of Dopamine D4 Receptorsin Motor Hyperactivity Induced by Neonatal 6–Hydroxydopamine Lesions in Rats," *McLean Division of MGH (Mailman Research Center)*.

*Primary Examiner*—Dwayne C. Jones
(74) *Attorney, Agent, or Firm*—Clark & Elbing LLP (57) ABSTRACT

A method of inhibiting motor hyperactivity in a mammal exhibiting the symptoms of attention deficit-hyperactivity disorder (ADHD) includes administering to a mammal a dopamine $D_4$ receptor-selective antagonist.

7 Claims, 8 Drawing Sheets

DOPAMINE D₄ RECEPTOR ANTAGONISTS AS TREATMENT FOR ATTENTION DEFICIT-HYPERACTIVITY DISORDER

CROSS REFERENCE TO RELATED APPLICATIONS

This application claims benefit of provisional application U.S. Ser. No. 60/275,198, filed Mar. 12, 2001, herein incorporated by reference.

This invention was made with support from the United States Government under USPHS (NIMH) Grant No. 1-R-01-MH-34006. The United States has certain rights in this invention.

BACKGROUND OF THE INVENTION

The invention relates to the role of dopamine $D_4$ receptors in behavioral hyperactivity. In particular, it relates to treatments and therapies for inhibiting motor hyperactivity and attentional dysfunction associated with attention deficit-hyperactivity disorder (ADHD).

Attention deficit-hyperactivity disorder (ADHD) is a prevalent neuropsychiatric syndrome that affects 2%–5% of school-aged boys, an uncertain proportion of girls, and some adults. See R. A. Barkley, *Attention Deficit Hyperactivity Disorder: A Handbook for Diagnosis and Treatment* (Guilford Press, New York, 1990). ADHD is characterized by excesses of hyperactive, inattentive and impulsive behavior. For several decades, the primary treatment available has been with psychostimulants for dopamine-enhancing effects, such as methylphenidate (Ritalin®) and amphetamines. Clinical use of these drugs is unsatisfactory owing to their short-lived benefits, risk of impaired sleep and appetite, of abnormal movements, and of abuse and illicit trade. See Goldman et al., *JAMA*, 279:1100 (1998).

An important action of stimulants is to enhance the functional activation of the amine neurotransmitter dopamine in the brain. See B. B. Hoffman and R. J. Lefkowitz in *The harmacological Basis of Therapeutics*, Chapter 10, Eds. Goodman and Gilman, McGraw-Hill, New York (1996). Dopamine (DA) is an important neurotransmitter involved in motor control, endocrine function, reward cognition and emotion. Dopamine modulates physiological processes though activation of five G-protein coupled receptors of the $D_1$-like ($D_1$ and $D_5$) and the $D_2$-like ($D_2$, D3, and $D_4$) receptor families. See K. A. Neve and R. L. Neve, in *The Dopamine Receptors*, K. A. Neve, R. L. Neve, Eds.; Humana Press, Totawa, N.J., 1997; pp. 27–76. $D_4$ receptors have received much attention, in part, because some atypical antipsychotics, notably clozapine, bind to $D_4$ receptors with higher affinity than to the more prevalent $D_2$ receptors. See H. H. M. Van Tol et al., *Nature* 350:614 (1991); and Seeman et al. *Neuropsychopharmacology* 16:93 (1997).

Human $D_4$ receptors occur in multiple forms with 2–11 copies of a 16-amino acid (48 base pair) sequence in the putative third intracellular loop of the peptide sequence. See Neve and Neve, supra. Several recent genetic studies suggest associations between polymorphic variants of the $D_4$ receptor gene (D4DR) and ADHD. These studies are inconclusive, with various studies producing evidence for and against such an association, but converging evidence suggests that the $D_4$ receptor has a role in exploratory behavior and as a genetic susceptibility factor for attention deficit disorder.

Tarazi et al., in "Dopamine $D_4$ receptors: significance for psychiatry at the millennium", *Molecular Psychiatry*, 4:529 (November 1999), identify a number of $D_4$ receptor-selective antagonists and report on the behavioral effects of these agents in animal models for psychosis. Tarazi et al. report mixed results, with some antagonists showing an antipsychotic-like effect, while others did not.

Numerous investigations into the effects of selective $D_4$ receptor agonists and antagonists on a variety of physiological and neurological functions have drawn a complex picture of the effects of $D_4$ receptor-selective drugs and no clear picture has emerged as to the role of the $D_4$ receptor in these processes. See Tarazi et al., supra; Patel et al., *J. Pharmacol. Exp. Ther.*, 283(2):636 (November 1997); Bristow et al., *J. Pharmacol. Exp. Ther.*, 283(3):1256 (December 1997); Feldpausch et al., *J. Pharmacol. Exp. Ther.*, 286(1):497 (July 1998); P. A. Broderick and M. F. Piercey, *J. Neuro. Transm.*, 105(6–7):749 (1998); Sanner et al., *Bioorg. Med. Chem. Lett.*, 8(7):725 (April 1998); Jentsch et al., *Psychopharmacology (Berl)*, 142(1):78 (Feb 1999); Belliotti et al., *J. Med. Chem.*, 42(25):5181 (December 1999); and Okuyama et al., *Life Sci.*, 65(20):2109 (1999).

SUMMARY OF THE INVENTION

The present invention is based on the discovery that motor hyperactivity can be dose-dependently reversed by $D_4$ receptor-selective antagonists.

The invention features a method of inhibiting motor hyperactivity in a mammal exhibiting the symptoms of attention deficit-hyperactivity disorder (ADHD). The method includes administering to a mammal a dopamine $D_4$ receptor-selective antagonist.

The $D_4$ receptor-selective antagonists are selected from the group consisting of PNU-101958, RBI-257, NGD-94-1, L-745,870, L-750,667, PD-172,938, PNU-101387G, S-18126, NRA-0045, CP-293,019, YM-43611 AND YM-50001, the structures of which are shown in Table 1. Preferred $D_4$ receptor-selective antagonist are CP-293,019 (7R,S-(4-fluoro-phenoxymethyl)-2-(5-fluoro-pyrimidin-2-yl)-octahydropyrido[1,2-α]pyrazine) and L-745,870(3-{[4-(4-chlorophenyl)piperazin-1-yl]methyl}-1H-pyrrolo[2,3-b] pyridine, based on their high selectivity for $D_4$ over $D_2$ receptors.

The $D_4$ receptor antagonist is administered intramuscularly, intravenously or subcutaneously to the mammal, and may be administered together with a pharmaceutically acceptable carrier. Preferred mammals include humans.

$D_4$ receptor-selective antagonists are expected to be superior to the conventional therapies using psychostimulants in that they do not stimulate dopamine release or block its inactivation by reuptake or transport. This expectation is supported by the observation that $D_4$ receptor-selective antagonists do not affect motor activity in healthy rats. See Bristow et al., supra; and Okuyama et al., supra. Furthermore, selectivity for $D_4$ receptors over $D_2$ receptors is desirable because interaction with $D_2$ receptors causes unwanted extrapyramidal and neuroendrocrine side effects.

By "$D_4$ receptor-selective antagonist" is meant an antagonist having more than 100, 200, 300, 500, 700, or 1,000 fold greater affinity for $D_4$ receptors than for $D_2$ receptors. Affinities for $D_4$ and $D_2$ receptors are determined using standard in vitro assays. See, for example, Den Hartog et al., U.S. Pat. No. 6,335,326, Patel et al., *J. Pharmacol. Exp. Ther.* 283:636–647 (1997), and Sanner et al., *Bioorg. Med. Chem. Lett.*, 8(7):725 (April 1998).

BRIEF DESCRIPTION OF THE DRAWING

The invention is described with reference to the figures, which are presented for the purpose of illustration only and are not intended to be limiting of the invention.

DETAILED DESCRIPTION OF THE INVENTION

We have found that motor hyperactivity can be dose-dependently reversed by $D_4$ receptor-selective antagonists. $D_4$-selective agonist, in contrast, exacerbates lesion-induced hyperactivity. $D_4$ receptors in ADHD model animals were increased (up-regulated) even more than $D_2$ receptor, and in a manner that closely correlated with motor hyperactivity, indicating that $D_4$ receptor-selective antagonists should be useful in the treatment of ADHD.

We have also found that the behavioral effects of the $D_4$ receptor-selective antagonists were not mediated by increased release of serotonin (5-hydroxytryptamine, 5-HT), an endogenous compound in the brain that may mediate the motor-inhibiting effects of stimulant drugs used in conventional ADHD treatment. These findings indicate that selective $D_4$ receptor antagonists alleviate lesion-induced hyperactivity by a mechanism distinct from that of stimulant drugs.

Several selective $D_4$ receptor antagonists have been recently identified and may be used in the invention. See Tarazi et al.; Sanner et al.; Belliotti et al; and Okuyama et al., supra. A non-limiting list of selective $D_4$ receptor antagonists is found in Table 1. A particularly preferred antagonist is 7R,S-(4-fluoro-phenoxymethyl)-2-(5-fluoro-pyrimidin-2-yl)-octahydropyrido[1,2-α]pyrazine, known as CP-293,019. CP-293,019 is a highly $D_4$ receptor-selective, full antagonist with more than 1000-times greater potency at $D_4$ receptors than at $D_2$ or other DA receptors, with negligible affinity for non-dopaminergic receptors except for moderate or low potency at serotonin 5-$HT_{1A}$ and 5-$HT_{2A}$ receptors ($K_i$=150 and 500 μM, respectively). See Sanner et al., supra. CP-293,019 can be used to treat humans with ADHD.

Another antagonist that can be used to treat humans with ADHD is 3-{[4-(4-chlorophenyl)piperazin-1-yl]methyl}-1H-pyrrolo[2,3-b]pyridine known as L-745,870. L-745,870 is also a highly selective fill antagonist for $D_4$ receptors. See Patel et al. *J. Pharmacol. Exp. Ther.* 283:636–647 (1997).

Selective $D_4$ Antagonists

PNU-101958

RBI-257

NGD 94-1

L-745,870

L-750,667

PD-172,938

Suitable D$_4$ receptor-selective candidate antagonists for use in the treatment of motor hyperactivity may be readily identified using routine and well-established methods. For example, behavioral studies of juvenile rats with neonatal 6-hydroxydopamine (6-OHDA) lesions, as is described below, can be used to screen drugs in order to identify candidate drugs for use in the method of the invention. Juvenile rats with neonatal 6-OHDA lesions of the brain that selectively destroy DA projections to the forebrain exhibit several characteristics that resemble the core symptoms of ADHD, most notably motor hyperactivity that occurs during the periadolescent period and gradually declines as lesioned rats mature. The motor hyperactivity seems to be due to deficient adaption to environmental stimuli, and can be dose-dependently antagonized by psychostimulants that are commonly used to alleviate symptoms of ADHD. As a result, juvenile rats with neonatal 6-OHDA lesions are accepted as a laboratory model for ADHD.

The selective D$_4$ receptor antagonist may be administered at therapeutically effective levels using conventional methods. The antagonist may be administered orally, intramuscularly, intravenously or subcutaneously to the patient. The antagonist may be administered together with a pharmaceutically acceptable carrier or other excipients known in the pharmaceutical art.

The following experimental results illustrate the invention; they are not meant to limit the invention in any way.

Experimental Results

Behavioral responses of 6-OHDA lesioned rats to D$_4$-selective drugs were investigated.

On postnatal day (PD) 5, male Sprague-Dawley rat pups randomly received intracisternal injections of vehicle ("sham-lesioned") (0.9% NaCl containing 0.1% ascorbic acid) or 6-OHDA hydrobromide ("lesioned") (100 $\mu$g free base) into the brain under hypothermal anesthesia at 45 min after pretreatment with desipramine hydrochloride (20 mg/kg free base) injected subcutaneously (s.c.). Lesions of DA in forebrain tissue sections were verified by quantifying DA transporter binding with [$^3$H]GBR-12935 (1-[2-(diphenylmethoxy)ethyl]-4-(3-phenylpropyl)piperazine) by computed autoradiography at the completion of experiments as an indication of loss of DA nerve terminals in forebrain.

Behavioral effects of neonatal lesions were examined by monitoring locomotor activity at PD 21–30 in a novel environment to provoke exploratory activity. Rats were maintained under a 12-h artificial daylight/dark schedule (on, 07:00–19:00 h), with free access to tap-water and standard rat chow. Motor activity was automatically monitored for 90 min between PD 21 and 30, with a computer-controlled photobeam activity monitoring system (San Diego Instruments, San Diego, Calif.). Testing was carried out in a novel testing environment (17×8×8 inch transparent plastic cages with 4×8 horizontal infrared beams) between 10:00 and 16:00 h in the temporary absence of food and water. Test agents were dissolved in 0.9% saline or 35% 2-hydroxypropyl- cyclodextrin, and given intraperitoneally (i.p.) in randomized sequence immediately prior to testing. Sessions were separated by 48 hours. Some rats receiving CP-293,019 were pretreated with the serotonin receptor blocker methysergide (2 mg/kg, i.p.) 30 min prior to behavioral testing. Breaking of consecutive photobeams was scored as locomotion.

Figure 1A:
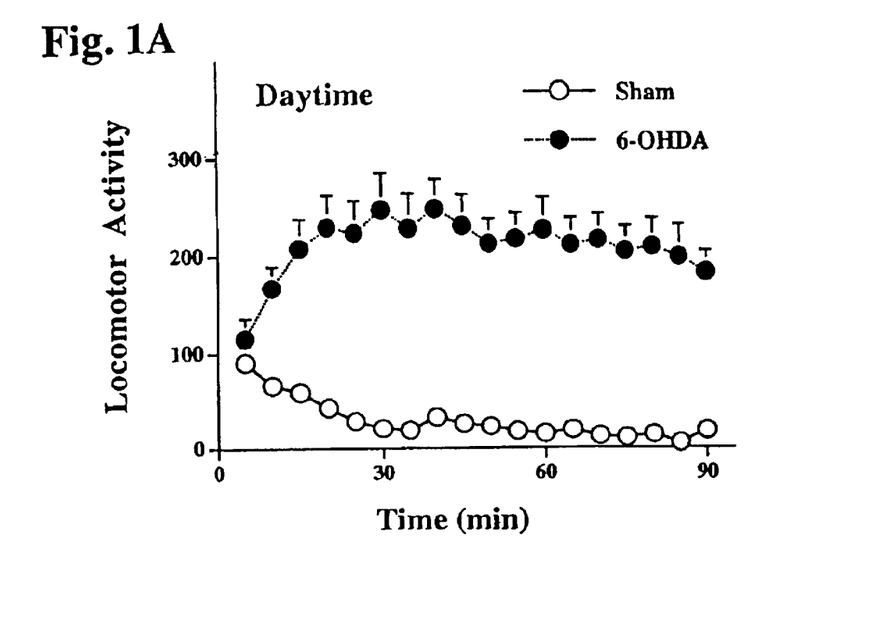
FIG. 1 plots the locomotor activity of sham-lesioned (control) rats (○) and 6-OHDA-lesioned rats (•) over a 90 minute observation period for (A) Daytime activity, at 10:00–16:00h (N=23); and (B) Nocturnal activity, 22:00–04:00h (N=17).
Figure 1B:
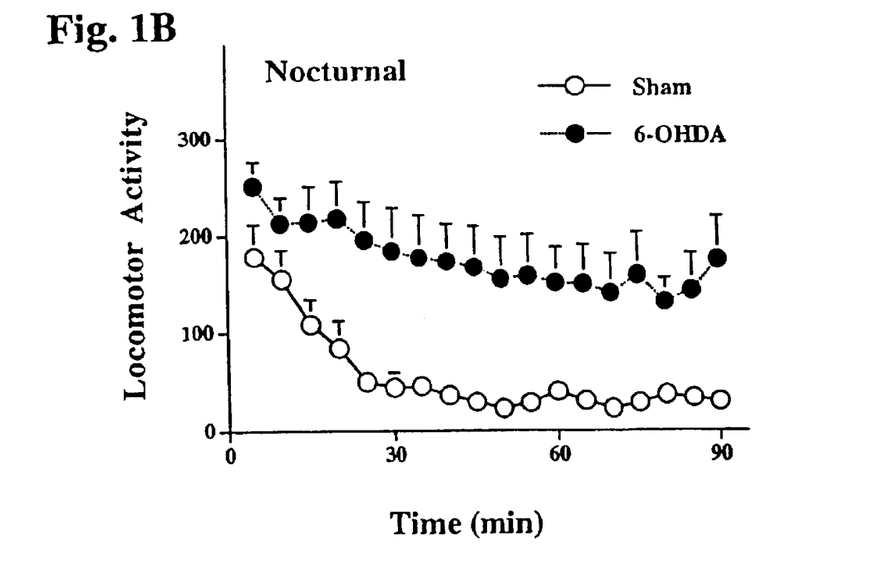
Figure 2A:
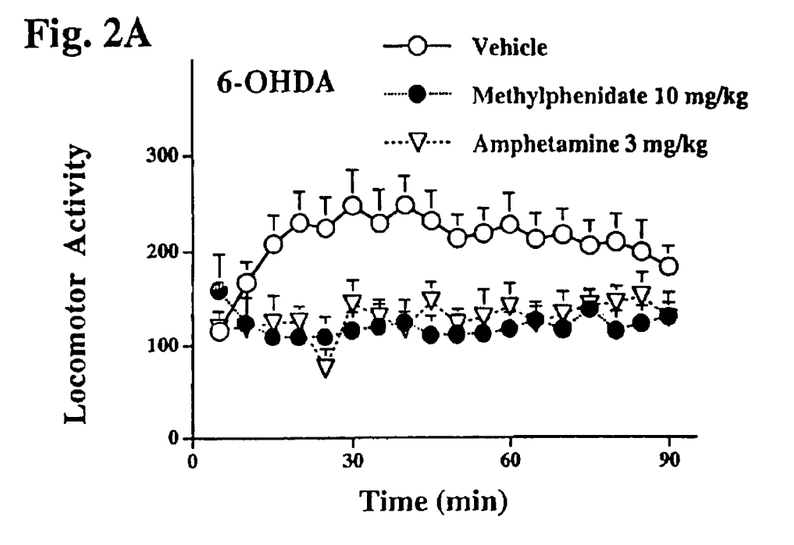
FIG. 2 shows the effect of psychostimulants in (A) 6-OHDA-lesioned rats (10:00–16:00h; N=14–23), and (B) sham-lesioned rats (10:00–16:00h, N=12) and is a plot of the locomotor activity of rats without psychostimulant (○), with administration of methylphenidate (●), and with administration of amphetamine (▽).
Figure 2B:
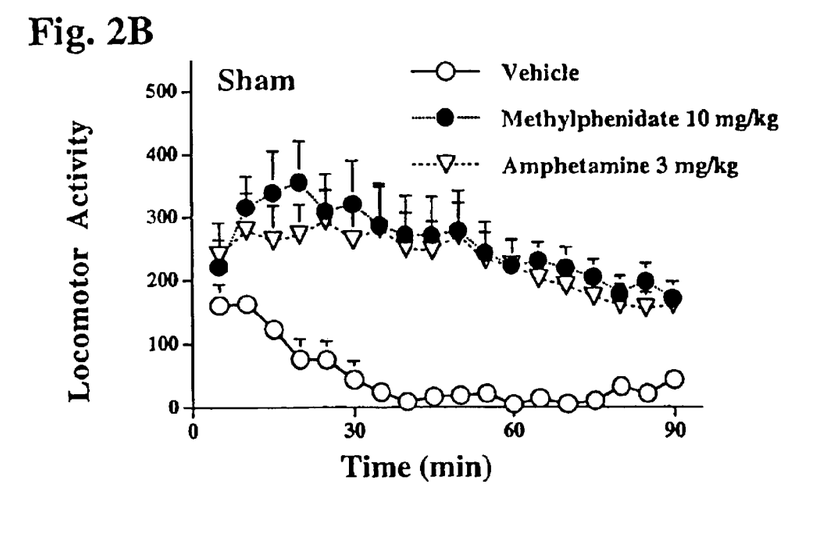

Lesioned rats exhibited much higher spontaneous activity than sham-lesioned littermate controls during both daytime and nocturnal testing (FIGS. 1A and 1B). As is shown in FIGS. 1A and 1B, motor activity of lesioned rats did not differ significantly from controls for the first 5–10 min of testing, but failed to decline throughout the 90 min session, long after arousal in control rats had greatly diminished. This temporal pattern indicated that lesioned rats are deficient in adaptation to behaviorally effective ambient stimuli in a novel environment. As expected, hyperactivity in lesioned rats was reduced by (+)-amphetamine and (±)-methylphenidate (FIG. 2A), which is consistent with clinical administration of psychostimulants in patients with ADHD. In contrast to their motor-inhibiting effects in lesioned rats, both psychostimulants greatly increased motor activity in sham-lesioned controls (FIG. 2B).

Rats were sacrificed 2 days after the last behavioral testing for autoradiographic analysis of DA receptor density. Frozen coronal brain sections (10 $\mu$m) were prepared in a cryostat at −17° C., thaw-mounted on gelatin-coated microscopic slides and stored at −80° C. until quantitative autoradiographic assays. D$_2$-like receptor binding was assayed with 1 nM [$^3$H]nemonapride in the presence of 0.5 $\mu$M 1,3-ditolylguanidine and 0.1 $\mu$M pindolol to block 5-HT$_{1A}$ sites in the brain tissue. Nonspecific binding was determined with 10 μM 5(−)-sulpiride. $D_4$ receptor density was assayed similarly using [$^3$H]nemonapride, but in the presence of raclopride in a concentration that selectively masks $D_2$ and $D_3$ but not $D_4$, receptors. $D_1$-like receptors were assayed with 1.0 nM [$^3$H]SCH-23390 in the presence of 40 nM ketanserin to mask 5-$HT_{2A/2C}$ receptor sites. Nonspecific binding was determined with 1 μM cis-flupenthixol.

Neonatal 6-OHDA lesions significantly increased $D_4$ receptor binding in caudate-putamen tissue (CPu; lateral: 40.3%; medial: 35.2%), but not in nucleus accumbens (NAc) or prefrontal cerebral cortex (PFC). $D_2$-like ($D_2/D_3/D_4$) receptor binding also was increased in CPu, and not in NAc and PFC by the lesions. The magnitude of increase of $D_2$-like receptors (16.6% and 18.3% in lateral and medial CPu, respectively) was about half of that of $D_4$ receptors. $D_1$-like receptor binding was unchanged in CPu, NAc and PFC by neonatal 6-OHDA lesions. These results are reported in Table 2, which shows the specific receptor binding of sham and lesioned rats. Specific binding data are reported in fmol/mg tissue± SEM. Data indicated by [*] or [**] demonstrate a statistically significant difference between binding for sham-lesioned and 6-OHDA lesioned rats.

TABLE 2

Effects of neonatal 6-OHDA lesions on dopamine receptor binding in rat forebrain.

| | $D_1$-like | | $D_2$-like | | $D_4$ | |
|---|---|---|---|---|---|---|
| | Sham | 6-OHDA | Sham | 6-OHDA | Sham | 6-OHDA |
| CPu/Lateral | 253.6 ± 13.7 | 228.5 ± 11.6 | 194.3 ± 9.8 | 226.5 ± 7.2* | 20.6 ± 2.2 | 28.9 ± 1.4** |
| CPu/Medial | 244.1 ± 14.3 | 233.4 ± 11.8 | 133.3 ± 6.8 | 157.7 ± 6.0* | 14.2 ± 1.5 | 19.2 ± 1.7** |
| NAc | 167.9 ± 10.4 | 173.9 ± 9.7 | 114.6 ± 8.2 | 102.2 ± 6.5 | 14.0 ± 1.2 | 15.0 ± 1.6 |
| PFC | 6.3 ± 2.4 | 39.0 ± 2.3 | 9.8 ± 0.4 | 10.3 ± 0.5 | 2.0 ± 0.4 | 2.0 ± 0.2 |

*By ANOVA: $p < 0.05$
**By ANOVA: $p < 0.01$

Figure 3:
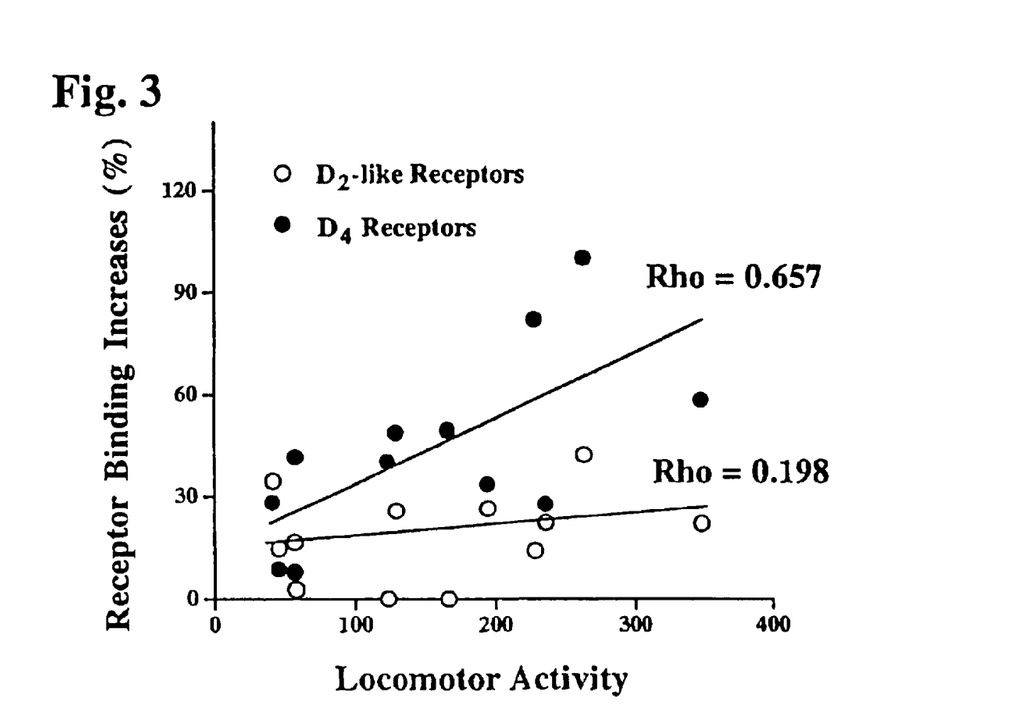
FIG. 3 is a plot of percent increase in receptor binding vs. locomotor activity for $D_2$-like receptors (○) and $D_4$ receptors (●), which shows the relationship between motor hyperactivity and changes of dopamine receptor binding in CPu of 6-OHDA-lesioned rats analyzed by Spearman Rank Correlationship for N=12.

Lesion-induced hyperactivity was strongly correlated with increases in $D_4$ receptor binding in CPu in individual rats but not with increases in of $D_2$-like receptors. This is illustrated graphically in FIG. 3.

Figure 4A:
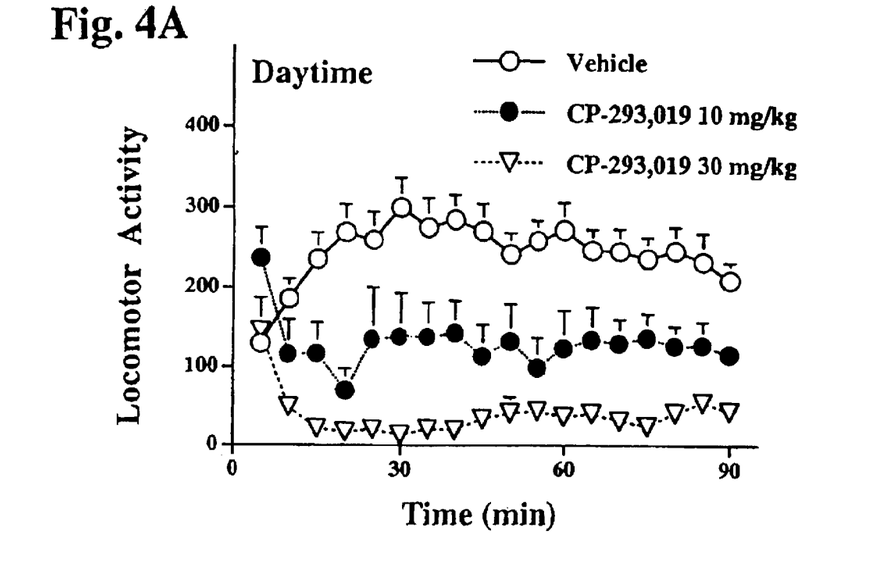
FIG. 4 is plot of the locomotor activity of 6-OHDA-lesioned rats over a 90 minute observation period without $D_4$ antagonist (○); and at a low dosage (●) and high dosage (▽) of CP-293,019 for (A) Daytime activity, 10:00–16:00h (N=23); and (B) Nocturnal activity, 22:00–04:00h (N=13).
Figure 4B:
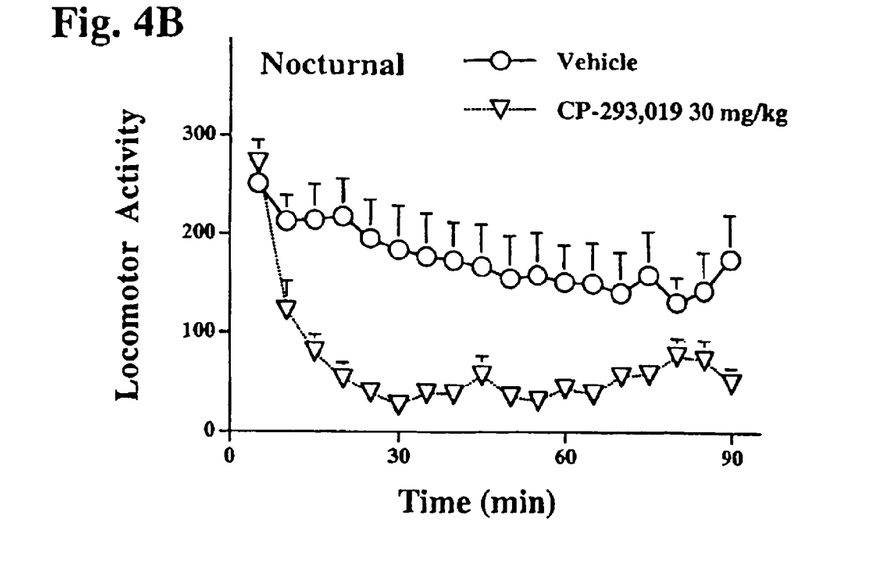

To assess the functional significance of the up-regulated $D_4$ receptors for motor hyperactivity induced by neonatal lesions, behavioral effects of representative $D_4$ receptor antagonist and agonist drugs were examined. CP-293,019 was chosen for this study because it is a highly $D_4$ receptor-selective, full antagonist with negligible affinity for non-dopaminergic receptors. When locomotor activity was measured as described above for sham- and 6-OHDA-lesioned rats, the $D_4$ receptor antagonist demonstrated dose-dependent mitigation of lesion-induced hyperactivity (FIG. 4A). At a dose of 10 mg/kg (i.p.), motor activity in lesioned rats was inhibited by approximately 40%, and at 30 mg/kg, it was indistinguishable from sham-lesioned controls. Nocturnal hyperactivity (equivalent to daytime activity in humans) also was completely reversed by CP-293,019 at 30 mg/kg in lesioned rats (FIG. 4B).

Figure 5:
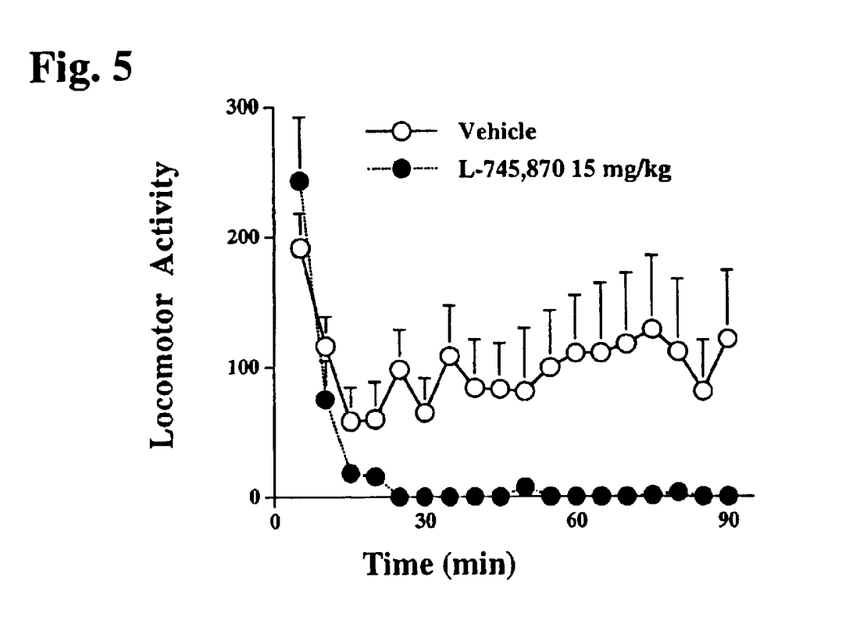
FIG. 5 is a plot of the locomotor activity of 6-OHDA-lesioned rats over a 90 minute observation period without antagonist (○); with L-745,870 (●), 10:00–16:00h(N=9).

Another highly $D_4$-selective antagonist L-745,870 was also examined. At a dose of 15 mg/kg (i.p.), motor activity in lesioned rats was reversed to a level similar to that found in control rats (FIG. 5).

Figure 6:
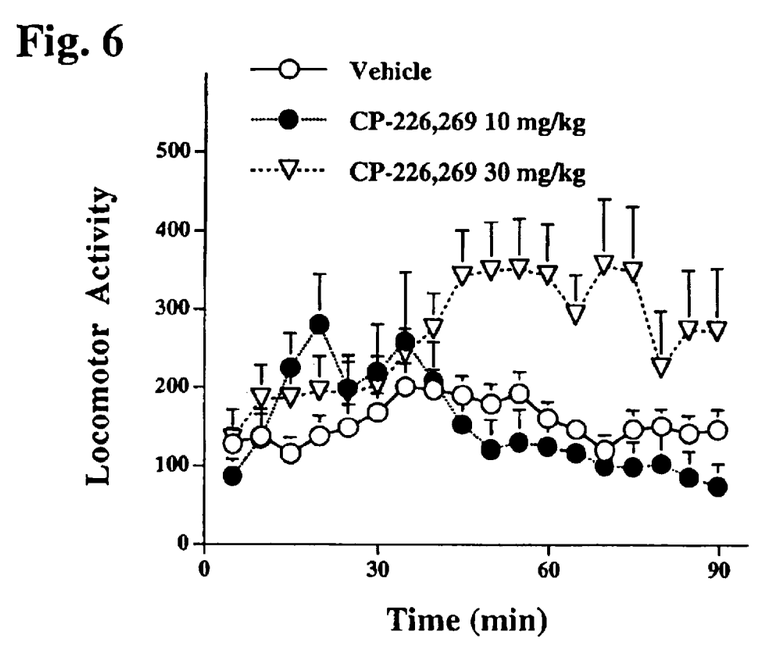
FIG. 6 is a plot of the locomotor activity of 6-OHDA-lesioned rats over a 90 minute observation period without $D_4$ agonist (○); and at a low dosage (●) and high dosage (▽) of CP-226,269, a selective $D_4$ receptor agonist, 10:00–16:00h (N=17).
Figure 7:
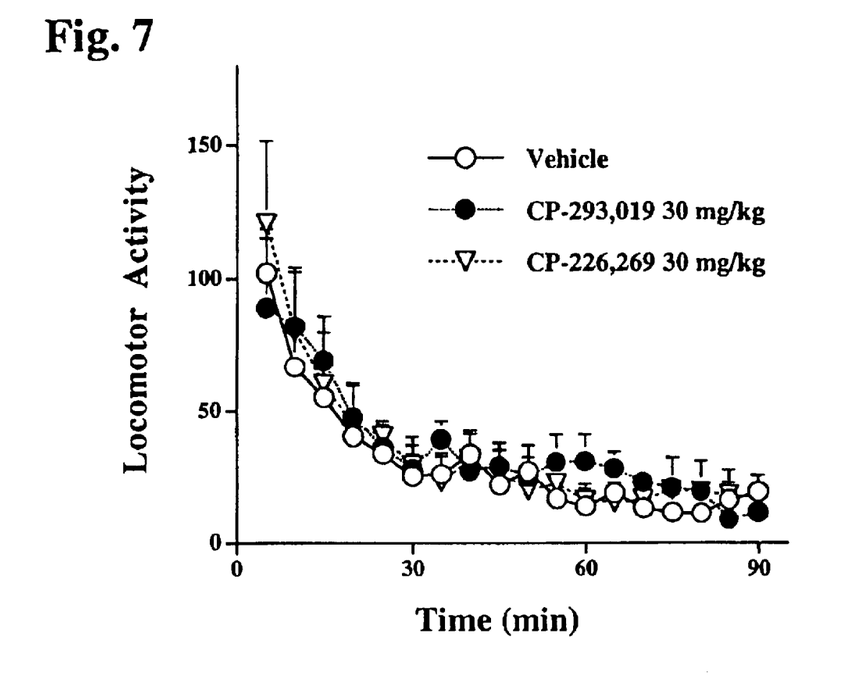
FIG. 7 is a plot of the locomotor activity of sham-lesioned rats over a 90 minute observation period without added drug (○); with CP-293, 019 (●) and with CP-226,269 (▽), 10:00–16:00h (N=17).

In striking contrast to the effects of CP-293,019 and L-745,870, a highly $D_4$-selective agonist, CP-226,269, produced dose-dependent exacerbation of lesion-induced hyperactivity (FIG. 6). Neither $D_4$-agent (agonist or antagonist) affected motor activity in sham-lesioned controls (FIG. 7). This result is in contrast to psychostimulants that increase hyperactivity in control rats. See FIG. 2B. These findings suggest that $D_4$ receptors may be functionally dormant under normal conditions, but activated by DA denervation at a critical developmental period.

Figure 8:
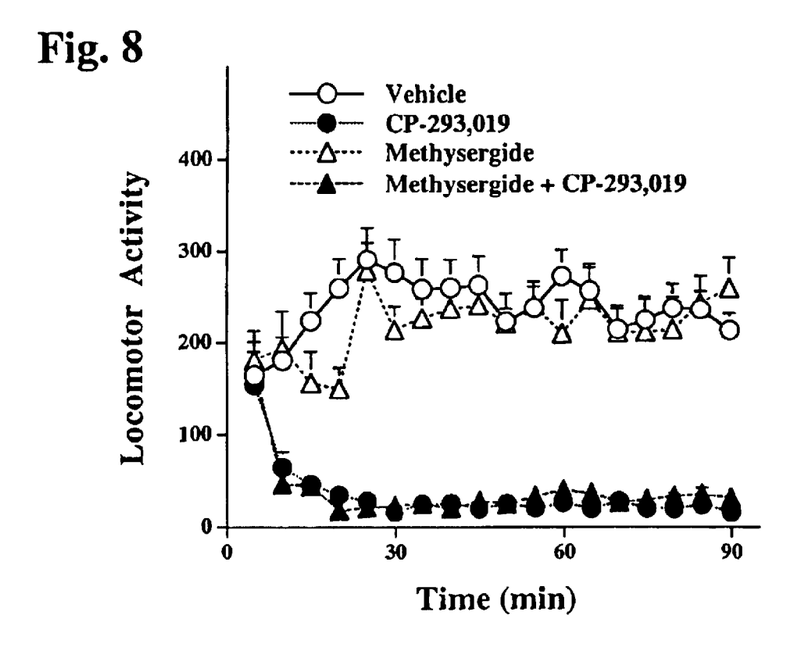
FIG. 8 is a plot of the locomotor activity of 6-OHDA-lesioned rats over a 90 minute observation period without $D_4$ agonist (○); with methysergide (Δ) (2 mg/kg administered 30 min prior to testing), with CP-293,019(●) (30 mg/kg); and with both methysergide and CP-293,019 (▲), which shows the absence of an effect of methysergide pretreatment on motor-inhibiting effects.

In addition to blocking or reversing neuronal transport of DA, stimulant drugs also release 5-HT. In hyperactive juvenile rats with neonatal 6-OHDA lesions as well as in hyperactive DA-transporter genetic knockout mice, the motor-inhibiting effects of stimulants seem to be mediated by enhanced release of 5-HT. Therefore, we tested the possibility of interaction of $D_4$-selective antagonists with 5-HT neurotransmission by using methysergide, a broad-spectrum 5-HT receptor antagonist. Pretreatment of 6-OHDA-lesioned rats with methysergide did not affect their motor responses to subsequent injection of CP-293,019 (FIG. 8), suggesting that the behavioral effects of the $D_4$ antagonists were not mediated by increased release of 5-HT. Methysergide alone failed to affect lesion-induced hyperactivity, further indicating that the motor-inhibiting effects of $D_4$-selective antagonists in lesioned rats were not due to affinity for 5-HT receptors.

A contribution of $D_2$ receptor blockade to the behavioral effects of $D_4$-selective antagonists seems unlikely since this agent interacts very weakly at $D_2$ receptors. These findings indicated that $D_4$-selective antagonists antagonize lesion-induced hyperactivity by a mechanism distinct from that of stimulant drugs.

Those skilled in the art will recognize or be able to ascertain with no more than routine experimentation many equivalents to the specific embodiments of the invention described herein. All patents and publications referenced herein are hereby incorporated in their entirety by reference.

We claim:

1. A method of inhibiting motor hyperactivity in a mammal exhibiting the symptoms of attention deficit-hyperactivity disorder, said method comprising administering to said mammal a dopamine D4 receptor-selective antagonist having a more than 200 fold greater affinity for D4 receptors than for D2 receptors.

2. The method of claim 1, wherein said D4 receptor-selective antagonist has more than 500 fold greater affinity for D4 receptors than for D2 receptors.

3. A method of inhibiting motor hyperactivity in a mammal exhibiting the symptoms of attention deficit-hyperactivity disorder, said method comprising administering to said mammal a dopamine D4 receptor-selective antagonist selected from the group consisting of PNU-101958, RBI-257, NGD-94-1, L-745,870, L-750,667, PD-172,938, PNU-101387G, S-18126, NRA-0045, CP-293,019, YM-43611 AND YM-50001.

4. The method of claim 3, wherein said $D_4$ receptor-selective antagonist is CP-293,019.

5. The method of claim 3, wherein said $D_4$ receptor-selective antagonist is L-745,870.

6. The method of claim 3, wherein said $D_4$ receptor-selective antagonist is PNU-101958.

7. The method of any of claims 1–6, wherein said D4 receptor antagonist is administered intramuscularly, intravenously or subcutaneously.

* * * * *

UNITED STATES PATENT AND TRADEMARK OFFICE
CERTIFICATE OF CORRECTION

PATENT NO. : 6,747,029 B2
DATED : June 8, 2004
INVENTOR(S) : Baldessarini et al.

It is certified that error appears in the above-identified patent and that said Letters Patent is hereby corrected as shown below:

Column 1,
Line 38, replace "*harmacological*" with -- *Pharmacological* --; and
Line 44, replace "($D_2$, D3, and $D_4$)" with -- ($D_2$, $D_3$, and $D_4$) --.

Column 2,
Line 52, replace "neuroendrocrine" with -- neuroendocrine --.

Signed and Sealed this

Twelfth Day of April, 2005

JON W. DUDAS
*Director of the United States Patent and Trademark Office*